United States Patent
Ishihara et al.

(10) Patent No.: US 10,831,437 B2
(45) Date of Patent: Nov. 10, 2020

(54) SOUND SIGNAL CONTROLLING APPARATUS, SOUND SIGNAL CONTROLLING METHOD, AND RECORDING MEDIUM

(71) Applicant: YAMAHA CORPORATION, Hamamatsu (JP)

(72) Inventors: Atsushi Ishihara, Iwata (JP); Morito Morishima, Fukuroi (JP); Kiyoshi Yamaki, Iwata (JP); Takehiko Kawahara, Hamamatsu (JP)

(73) Assignee: YAMAHA CORPORATION, Hamamatsu (JP)

( * ) Notice: Subject to any disclaimer, the term of this patent is extended or adjusted under 35 U.S.C. 154(b) by 356 days.

(21) Appl. No.: 15/950,338

(22) Filed: Apr. 11, 2018

(65) Prior Publication Data

US 2018/0232197 A1 Aug. 16, 2018

Related U.S. Application Data

(63) Continuation of application No. PCT/JP2016/079921, filed on Oct. 7, 2016.

(30) Foreign Application Priority Data

Oct. 19, 2015 (JP) .................................. 2015-205263

(51) Int. Cl.
*A61M 21/02* (2006.01)
*G06F 3/16* (2006.01)
(Continued)

(52) U.S. Cl.
CPC ............ *G06F 3/165* (2013.01); *A61B 5/4812* (2013.01); *A61B 5/4836* (2013.01); *A61M 21/02* (2013.01);
(Continued)

(58) Field of Classification Search
CPC .......... A61M 21/02; A61M 2205/3303; A61B 5/4812
See application file for complete search history.

(56) References Cited

U.S. PATENT DOCUMENTS

| 8,550,978 | B2 | 10/2013 | Ullmann |
| 9,978,358 | B2 | 5/2018 | Morishima |
| 2009/0149699 | A1 | 6/2009 | Ullmann |

FOREIGN PATENT DOCUMENTS

| CN | 101060879 A | 10/2007 |
| JP | H04269972 A | 9/1992 |

(Continued)

OTHER PUBLICATIONS

Office Action issued in Japanese Appln. No. 2015-205263 dated Jul. 2, 2019. English translation provided.

(Continued)

*Primary Examiner* — Christine H Matthews
(74) *Attorney, Agent, or Firm* — Rossi, Kimms & McDowell LLP (57) ABSTRACT

An information processing apparatus includes: an estimator configured to estimate, based on biological information of a human subject, a sleep indicator indicative of a depth of sleep of the human subject; and a volume controller configured to control a volume adjuster that generates a second playback sound signal by adjusting an amplitude of a first playback sound signal, such that the first playback sound signal is adjusted based on the sleep indicator and a volume of an ambient sound in an environment in which the human subject is situated.

5 Claims, 8 Drawing Sheets

(51) Int. Cl.
*G06K 9/00* (2006.01)
*H04R 3/04* (2006.01)
*H04R 1/02* (2006.01)
*A61B 5/00* (2006.01)
*A61B 5/024* (2006.01)
*A61B 5/08* (2006.01)
*A61M 21/00* (2006.01)

(52) U.S. Cl.
CPC ....... *G06K 9/0053* (2013.01); *G06K 9/00543* (2013.01); *G06K 9/00892* (2013.01); *H04R 1/028* (2013.01); *H04R 3/04* (2013.01); *A61B 5/024* (2013.01); *A61B 5/0816* (2013.01); *A61B 5/6892* (2013.01); *A61B 5/7415* (2013.01); *A61B 2560/0242* (2013.01); *A61M 2021/0027* (2013.01); *A61M 2205/332* (2013.01); *A61M 2205/3303* (2013.01); *A61M 2205/3306* (2013.01); *A61M 2205/3331* (2013.01); *A61M 2205/3375* (2013.01); *A61M 2205/3553* (2013.01); *A61M 2205/3569* (2013.01); *A61M 2205/3584* (2013.01); *A61M 2205/3592* (2013.01); *A61M 2205/502* (2013.01); *A61M 2205/505* (2013.01); *A61M 2205/52* (2013.01); *A61M 2230/06* (2013.01); *A61M 2230/10* (2013.01); *A61M 2230/30* (2013.01); *A61M 2230/42* (2013.01); *A61M 2230/63* (2013.01); *G06K 2009/00939* (2013.01); *H04R 2430/01* (2013.01)

(56) References Cited

FOREIGN PATENT DOCUMENTS

| | | |
|---|---|---|
| JP | H078558 A | 1/1995 |
| JP | 2008525055 A | 7/2008 |
| JP | 2014226361 A | 12/2014 |

OTHER PUBLICATIONS

International Search Report issued in Intl. Appln. No. PCT/JP2016/079921 dated Dec. 20, 2016. English translation provided.
Written Opinion issued in Intl. Appln. No. PCT/JP2016/079921 dated Dec. 20, 2016.
Office Action issued in Chinese Appln. No. 201680060969.5 dated Oct. 9, 2019. English translation provided.

SOUND SIGNAL CONTROLLING APPARATUS, SOUND SIGNAL CONTROLLING METHOD, AND RECORDING MEDIUM

BACKGROUND OF THE INVENTION

Field of the Invention

The present invention relates to a technique for controlling a sound signal.

Description of the Related Art

In recent years, there has been proposed a technique that improves sleep or induces relaxation by detecting biological information such as body motion, breathing, and heartbeat, and generating sound in accordance with the detected biological information (e.g., Japanese Patent Application Laid-Open Publication No. H04-269972). There is also known a technique by which a sound volume is controlled in accordance with a depth of sleep in a system in which audio-signal reproduction also is controlled in accordance with a person's state of relaxation (e.g., Japanese Translation of PCT International Application Publication No. JP-T-2008-525055).

Generally, a sleep pattern of a person takes the form of light sleep and deep sleep in a certain rhythm, repeated four to five times a night at an approximately 90-minute cycle. During sleep, a user may hear sounds that include, in addition to a playback sound that leads the user to good sleep, ambient sound such as a sound of an air-conditioner in a room and outdoor traffic noise.

In the conventional technology, a volume of playback sound is determined without taking ambient sound into account. In such case, when it becomes difficult for a user to hear playback sound due to ambient sound, the playback sound cannot lead the user into a state of good sleep. Alternatively, in a case where the sleep of the user is light and where a combined total volume of playback sound and ambient sound exceeds a predetermined level, the user is awakened and prevented from good sleep.

SUMMARY OF THE INVENTION

The present invention has been created in view of the above circumstances, and an object thereof is to improve sleep of a human subject by controlling a playback sound signal while taking ambient sound into account.

In order to solve the stated problem, one aspect of a sound signal controlling apparatus according to the present invention includes: an estimator configured to estimate, based on biological information of a human subject, a sleep indicator indicative of a depth of sleep of the human subject; and a volume controller configured to control a volume adjuster that generates a second playback sound signal by adjusting an amplitude of a first playback sound signal, such that the amplitude is adjusted based on the sleep indicator and on a volume of ambient sound in an environment in which the human subject is situated.

One aspect of a sound signal controlling method according to the present invention includes: estimating, based on biological information of a human subject, a sleep indicator indicative of a depth of sleep of the human subject; and controlling a volume adjuster that generates a second playback sound signal by adjusting an amplitude of a first playback sound signal, such that the amplitude is adjusted based on the sleep indicator and on a volume of ambient sound in an environment in which the human subject is situated.

One aspect of a recording medium according to the present invention is a computer-readable recording medium having recorded thereon a program that causes a computer to execute: sleep indicator estimating processing of estimating, based on biological information of a human subject, a sleep indicator indicative of a depth of sleep of the human subject; and volume controlling processing of controlling a volume adjuster that generates a second playback sound signal by adjusting an amplitude of a first playback sound signal, such that the amplitude is adjusted based on the sleep indicator and on a volume of ambient sound in an environment in which the human subject is situated.

DESCRIPTION OF THE EMBODIMENTS

In the following, embodiments of the present invention will be described with reference to the accompanying drawings.

First Embodiment

Figure 1:
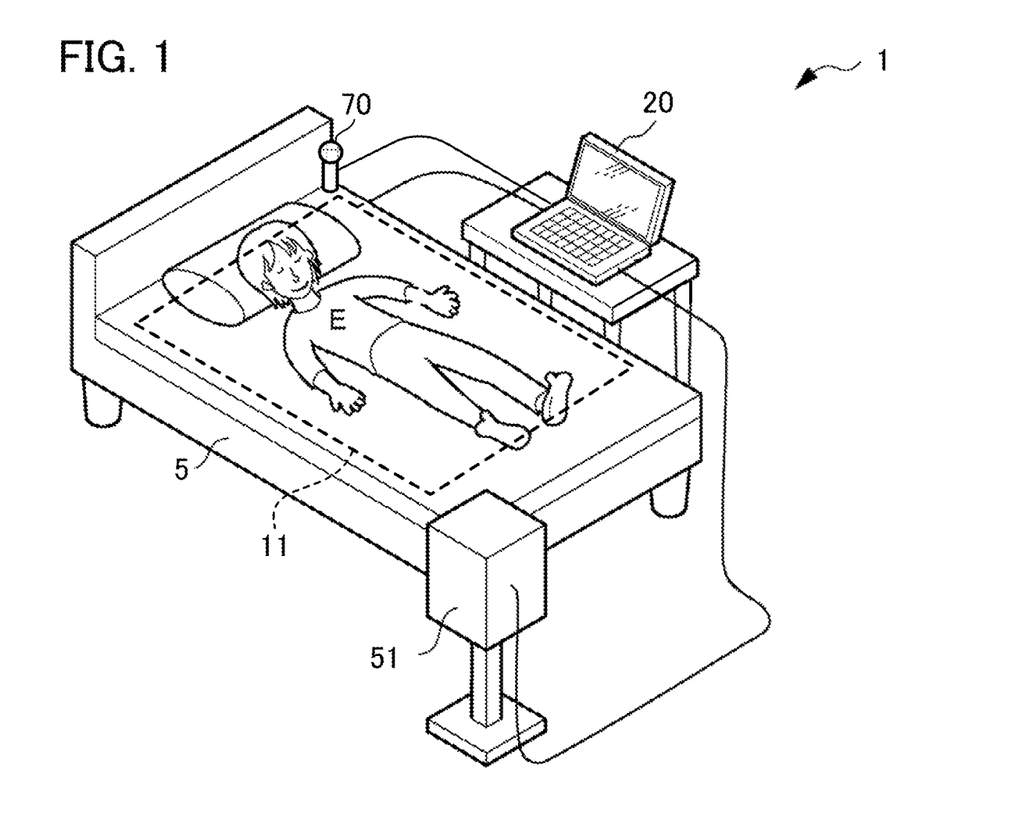
FIG. 1 is an illustration showing an overall configuration of a system that includes an information processing apparatus according to a first embodiment.

FIG. 1 is a diagram showing an overall configuration of a system 1 that includes an information processing apparatus 20 according to a first embodiment. As shown in the figure, the system 1 is configured to include a sensor 11, the information processing apparatus 20, a loudspeaker 51, and a microphone 70. The system 1 is intended to improve a quality of sleep of a human subject E lying on his/her back on a bed 5 by enabling the human subject E to hear sound (playback sound) emitted from the loudspeaker 51. The information processing apparatus 20 is able to play multiple pieces of sound information separately. The system 1 detects biological information of the human subject E with the sensor 11, and estimates the depth of sleep of the human subject E based on the detected biological information. In the system 1, the microphone 70 converts sound that the human subject E hears into a sound signal. The sound that the human subject E hears includes ambient sound in an environment in which the human subject E is situated, and playback sound (playback sound in accordance with sound information) emitted from the loudspeaker 51. The ambient sound, which is among the sound received by the microphone 70, is different from the playback sound. The system 1 adjusts a volume of the playback sound based on a depth of sleep of the human subject E and based on the ambient sound, such that the human subject E is able to hear the playback sound but will not wake up when he/she is in a state of light sleep.

The sensor 11 is formed of, for example, a sheet-like piezoelectric element, and is placed at a lower part of a mattress of the bed 5, for example. After the human subject E lies down on the bed 5, biological information of the human subject E is detected by the sensor 11. Body motion caused by biological activities including breathing and a heartbeat of the human subject E is detected by the sensor 11. The sensor 11 outputs a detected signal within which components (biological information) related to these biological activities are superimposed. For illustrative purposes, the figure shows a configuration in which detected signals are transmitted to the information processing apparatus 20 by wire. Alternatively, detected signals may be transmitted wirelessly.

The information processing apparatus 20 is able to acquire a breathing cycle BRm, a heartbeat cycle HRm, and body motion of the human subject E based on the detected signal (biological information) output from the sensor 11. The information processing apparatus 20 is, for example, a mobile terminal or a personal computer.

The loudspeaker 51 is arranged in such a way that sound is emitted toward the human subject E who is lying on his/her back on the bed 5. The loudspeaker 51 amplifies, with a built-in amplifier, a playback sound signal output from the information processing apparatus 20 and emits sound (playback sound) that is in accordance with the amplified playback sound signal. The microphone 70 is placed near a pillow. The microphone 70 converts sound heard by the human subject E into a sound signal, which is an electrical signal, and outputs the sound signal. The microphone 70 converts into the sound signal the sound that includes the playback sound, which is in accordance with the sound information, and ambient sound, such as a sound of an air-conditioner or outside vehicular traffic. In this embodiment, to emit playback sound that is in accordance with a playback sound signal generated based on sound information toward the human subject E from the loudspeaker 51 is referred to as "to play sound".

Figure 2:
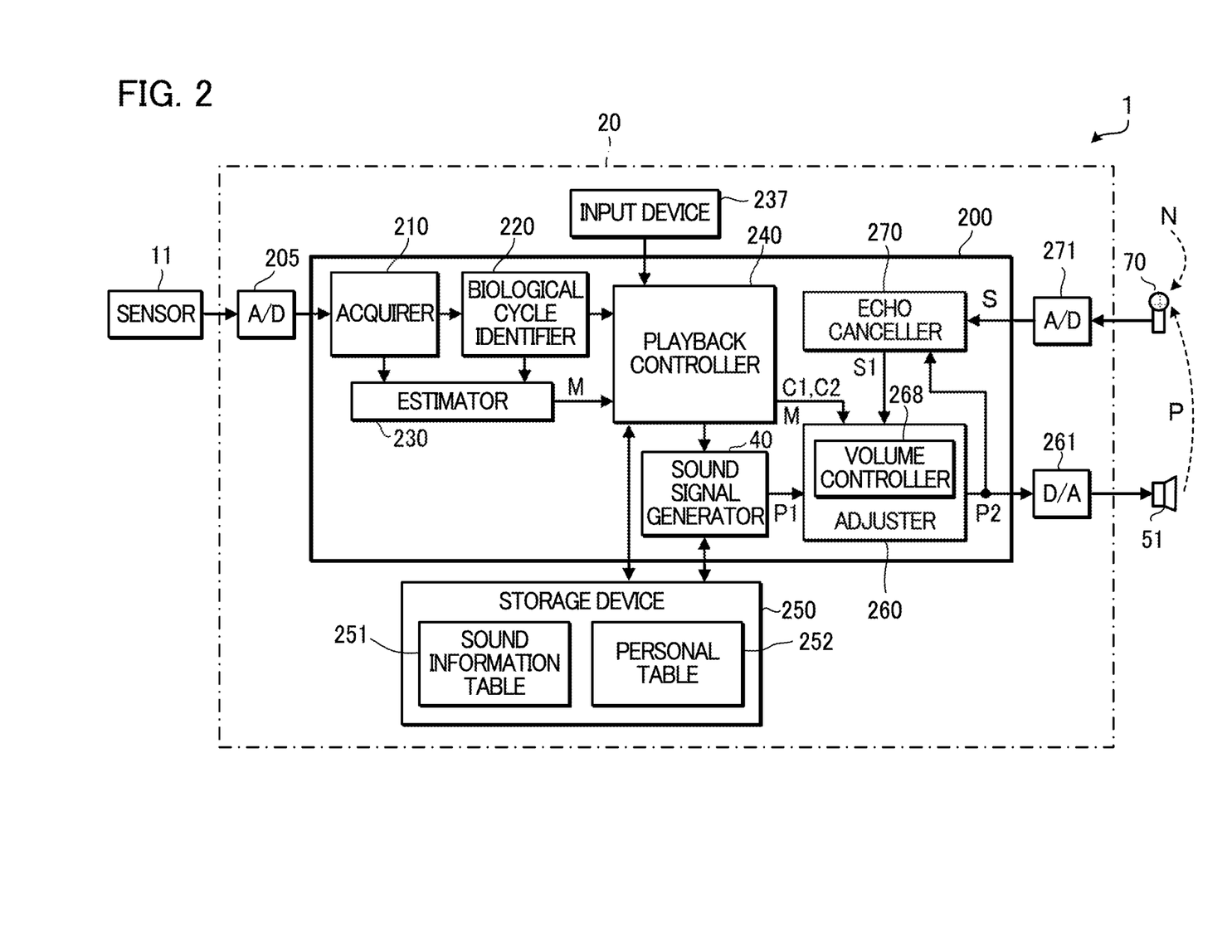
FIG. 2 is a block diagram showing a functional configuration of the information processing apparatus.

FIG. 2 is a block diagram showing a configuration of functional blocks mainly belonging to the information processing apparatus 20, among the elements in the system 1. As shown in the figure, the information processing apparatus 20 includes A/D converters 205 and 271, a controlling device 200, a storage device 250, a D/A converter 261, and an input device 237.

The storage device 250 is an example of a computer-readable recording medium. Furthermore, the storage device 250 is a non-transitory recording medium. The storage device 250 is a recording medium of any publicly known format, such as a semiconductor recording medium, a magnetic recording medium, or an optical recording medium. The storage device 250 may be a combination of these recording media. In this specification, a "non-transitory" recording medium encompasses all types of computer-readable recording media except for a recording medium, such as a transmission line, that temporarily records a transitory, propagating signal, and volatile recording media are not excluded.

The storage device 250 stores a program executed by the controlling device 200, a sound information table 251, and a personal table 252. The sound information table 251 stores multiple pieces of sound information. Here, sound information may be any data based on which a sound signal generator 40 (described later) can generate a playback sound signal. For example, sound information may be music performance data generated by converting music performance information into data, may be a parameter controlling the sound signal generator 40, or may be waveform data. In short, sound information is any information that is used to control the sound signal generator 40.

The controlling device 200 is formed by a processing device, such as a CPU. By retrieving the program stored in the storage device 250 and executing the program, the controlling device 200 serves as an acquirer 210, a biological cycle identifier 220, an estimator 230, a playback controller 240, the sound signal generator 40 that generates a first playback sound signal P1, an adjuster 260 that generates a second playback sound signal P2 by adjusting the first playback sound signal P1, and an echo canceller 270. Alternatively, all or a part of these functions may be realized by dedicated electronic circuitry. For example, the sound signal generator 40 may be formed by a LSI (large scale integration circuit).

The A/D converter 205 converts the detected signal output from the sensor 11 into a digital signal. The acquirer 210 stores the detected signal in a digital format in an internal memory, and then, outputs the digital detected signal to the biological cycle identifier 220 and to the estimator 230. The biological cycle identifier 220, based on the biological information included in the detected signal from the sensor 11, identifies the breathing cycle BRm and the heartbeat cycle HRm of the human subject E. The biological cycle identifier 220 outputs the breathing cycle BRm and the heartbeat cycle HRm of the human subject E to each of the estimator 230 and the playback controller 240. More specifically, the biological cycle identifier 220 extracts from the detected signal a frequency component that corresponds to a frequency range of human heartbeat. Then, the biological cycle identifier 220 executes a process that quantifies the frequency component using a predetermined threshold value, and identifies the heartbeat cycle HRm from the result of the process. A heartbeat component superimposed within the detected signal has smaller amplitudes than a breathing component superimposed within the detected signal. Thus, in a case where the biological cycle identifier 220 extracts the heartbeat component from the detected signal, the biological cycle identifier 220 may be conditioned to extract a component that has smaller amplitudes than the breathing component. The biological cycle identifier 220 extracts from the detected signal a frequency component that corresponds to a frequency range of human breathing. The biological cycle identifier 220 executes a process that quantifies the frequency component using a predetermined threshold value, and identifies the breathing cycle BRm from the result of the process. The breathing cycle BRm and the heartbeat cycle HRm are used as biological rhythms in the playback controller 240. Here, the biological cycle identifier 220 may identify a breathing rate BR per minute, instead of the breathing cycle BRm. The biological cycle identifier 220 may identify a heartbeat rate HR per minute, instead of the heartbeat cycle HRm. In other words, the biological cycle identifier 220 identifies heartbeat information related to heartbeat, and identifies breathing information related to breathing. The breathing information and the heartbeat information are used to control a tempo of a sound signal of heartbeat-linked sound generated in the sound signal generator 40, and to control a tempo of a sound signal of breathing-linked sound generated in the sound signal generator 40. The sound signal of the heartbeat-linked sound and the sound signal of the breathing-linked sound are included in the first playback sound signal P1. The breathing information and the heartbeat information correspond to parameters that control the sound signal generator 40. Information indicative of the heartbeat-linked sound and information indicative of the breathing-linked sound are each sound information and are stored in the sound information table 251. Here, it is assumed that the information indicative of the heartbeat-linked sound is waveform data having an amplitude envelope with a length close to a length of a heartbeat cycle; while the information indicative of the breathing-linked sound is waveform data having an amplitude envelope with a length close to a length of a breathing cycle. In this case, the playback controller 240 controls the sound signal generator 40 such that the sound signal generator 40 will repeatedly output, as a heartbeat-linked sound signal, waveform data that is information indicative of the heartbeat-linked sound for every heartbeat cycle HRm; and the sound signal generator 40 will repeatedly output, as a breathing-linked sound signal, waveform data that is information indicative of the breathing-linked sound for every breathing cycle BRm. In this way, the tempo (playback speed) of the heartbeat-linked sound and the tempo (playback speed) of the breathing-linked sound are controlled.

There exist a variety of ways to control the tempo of a sound in accordance with sound information. For example, waveform data with varying tempos may be prepared in advance, and the playback controller 240 may select, from among the waveform data with varying tempos, waveform data with a tempo that matches the heartbeat cycle HRm or the breathing cycle BRm. Alternatively, in a case where the sound information is music performance data, the playback controller 240 may control the sound signal generator 40 such that the tempo at which a sound signal is generated from the music performance data changes with the tempo of breathing or that of heartbeat.

The input device 237 is used by the human subject E to set various settings. The input device 237 is a touch panel or a keyboard. The input device 237 includes a start button, which the human subject E operates when he/she goes to bed, and a stop button, which the human subject E operates when he/she leaves bed. The human subject E is able to input information such as a wake-time by using the input device 237. The input device 237 is also used in a hearing ability test conducted prior to use of the system 1 by the human subject E.

In this embodiment, the estimator 230 estimates a sleep indicator M that indicates a depth of sleep of the human subject based on the biological information acquired by the acquirer 210. Sleep depth is an example of a sleep indicator M. The estimator 230 provides the sleep indicator M to the adjuster 260 through the playback controller 240. In this example, the estimator 230 estimates the sleep depth, which indicates the depth of sleep in which the state of the human subject E transits from resting to deep sleep and to waking, in the following seven stages: "Stand (going to bed or leaving bed)"; "Wake (wakefulness)"; "REM (REM sleep)"; "ST1 (first stage)"; "ST2 (second stage)"; "ST3 (third stage)"; and "ST4 (fourth stage)". In this example, the estimator 230 estimates a sleep depth indicating a depth of sleep at the seven stages. Alternatively, the estimator 230 may estimate the depth of sleep at five stages, wherein the first stage ST1 and the second stage ST2 are classified as "light sleep", and the third stage ST3 and the fourth stage ST4 are classified as "deep sleep".

More specifically, the estimator 230 estimates that a state of the human subject E is "going to bed or leaving bed" when body motion greatly changes immediately after the human subject E entering sleep or immediately prior to the human subject E awakening. The estimator 230 estimates that a state of the human subject E is "wakefulness" when the human subject E is at rest with relatively little body motion and a β-wave is dominant in a brain-wave pattern of the human subject E. The estimator 230 estimates that a state of the human subject E is "the first stage ST1 and the second stage ST2" when a θ-wave appears in the brain-wave pattern of the human subject E. The estimator 230 estimates that a state of the human subject E is "the third stage ST3 and the fourth stage ST4" when a δ-wave appears in the brain-wave pattern of the human subject E. The estimator 230 estimates that a state of the human subject E is "REM sleep" when a θ-wave appears in the brain-wave pattern of the human subject E and breathing is shallow and irregular. Any other known method may be used for estimating a depth of sleep.

Figure 3:
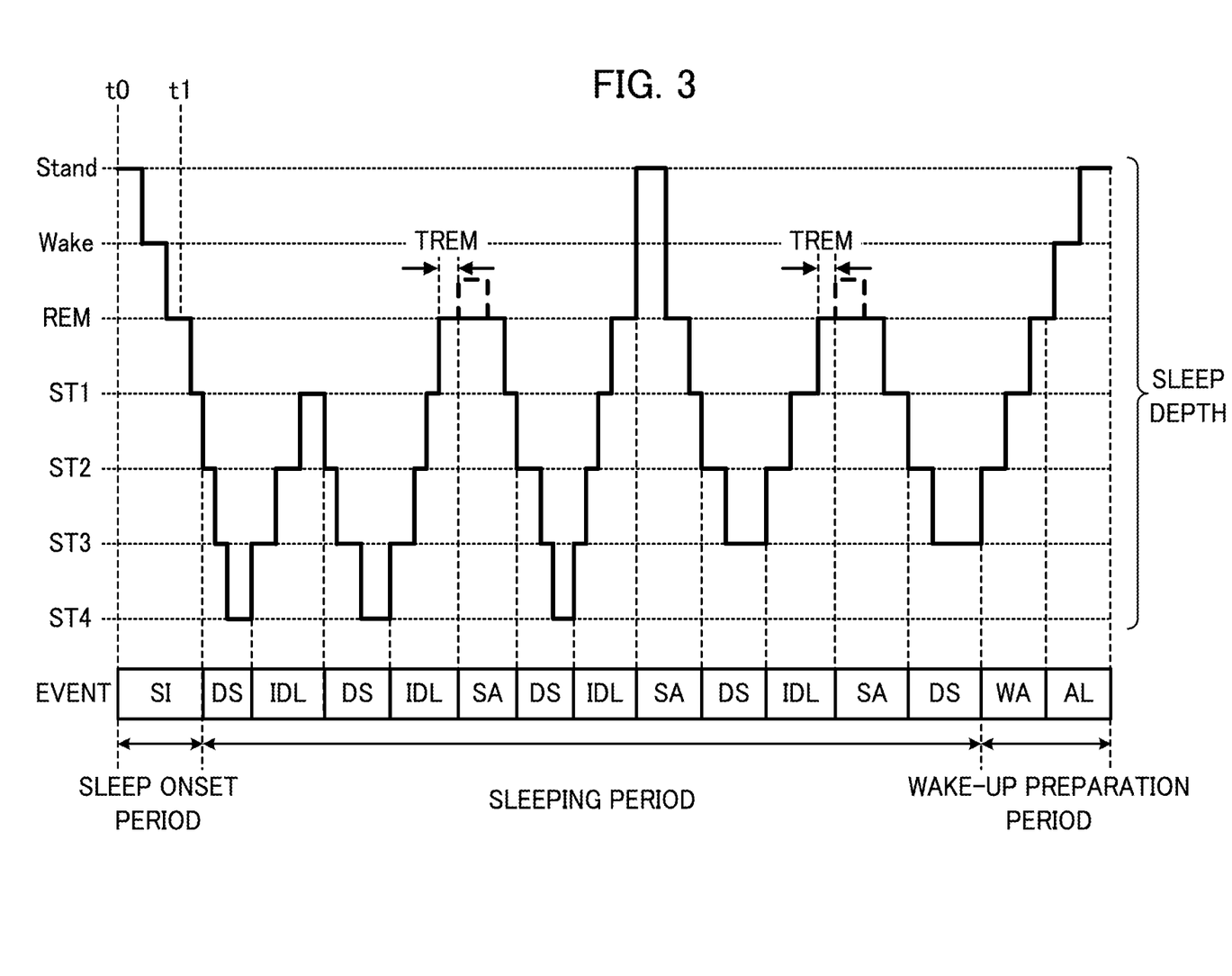
FIG. 3 is an explanatory diagram for describing a relationship between events and sleep depth.

In this embodiment, in order to lead the human subject E to good sleep, the playback controller 240 manages sound information to be played according to sleep sections, wherein the sleep sections are sections into which sleep of the human subject is divided along a time-axis according to temporal changes in the sleep depth during the sleep. More specifically, the playback controller 240 executes different events for different sleep sections by appropriately using sound information according to the sleep sections. As shown in FIG. 3, such events include: sleep onset induction SI (Sleepin); deep sleep induction DS (DeepSleep); waiting sequence IDL; awakening prevention SA (StopAwakening); awakening WA (WakeUp); and alarm AL (ALarm).

The sleep onset induction SI is executed to lead the human subject E into sleep during a period after the human subject E goes to bed till the sleep depth reaches the second stage ST2. The deep sleep induction DS is executed to lead the human subject E into deeper sleep during a period in which the sleep depth changes from the second stage ST2 to the fourth stage ST4 and a period in which the sleep depth is sustained at the fourth stage ST4. The waiting sequence IDL is executed following the deep sleep induction DS, and comes to an end after a predetermined length of time has passed since the onset of the waiting sequence IDL. After the waiting sequence IDL is executed, the sleep depth tends to transit from the fourth stage ST4 to a shallower depth of sleep. The awakening prevention SA is initiated when a time length TREM has passed after the sleep depth enters the REM sleep stage or a lighter sleep stage as the sleep depth becomes shallower. After a predetermined length of time has passed after the onset of the awakening prevention SA, or after the sleep depth reaches the second stage ST2, an event to be executed transits from the awakening prevention SA to the deep sleep induction DS. The awakening WA is initiated at a time point that is a time length TWS before an alarm setting time, and ends immediately before the alarm setting time. The alarm AL is executed from the alarm setting time until the human subject E operates the stop button. Here, the sleep onset induction SI corresponds to a sleep onset period, which is from a time point at which the human subject E goes to bed to a time point at which a depth of sleep reaches a level of deep sleep (the second stage ST2). The awakening WA and the alarm AL correspond to a wake-up preparation period, which is from the time point that is the time length TWS before the alarm setting time to a time at which the human subject E wakes up. The deep sleep induction DS, the waiting sequence IDL, and the awakening prevention SA correspond to a sleeping period, which is from the end of the sleep onset period to the beginning of the wake-up preparation period. The playback controller 240 divides sleep into a sleep onset period, a sleeping period, and a wake-up preparation period. The playback controller 240 provides a volume controller 268 with information necessary for the volume controller 268 to control the volume of playback sound depending on the period.

In general, a breathing cycle BRm and the heartbeat cycle HRm of a person tend to become longer during a period of transition from a calm state to deep sleep. During such a period, variations in these cycles tend to become smaller. Additionally, as sleep becomes deeper, there will be fewer body motions. In view of these tendencies, the estimator 230, based on the biological information acquired by the acquirer 210 and the breathing cycle BRm and the heartbeat cycle HRm identified by the biological cycle identifier 220, estimates a depth of sleep by combining a change in the breathing cycle BRm, change in the heartbeat cycle HRm, and a number of times the body moves per unit period and comparing the combined results with multiple threshold values. Alternatively, the estimator 230 may estimate a depth of sleep based on the heartbeat cycle HRm alone.

Sleep of a person can be broadly classified into REM sleep, in which sleep is light, and non-REM sleep, in which sleep is deep. Sleep of a person transits first to the non-REM sleep after he/she falls asleep, and then transits to light sleep, the REM sleep. In sleep of a person, two types of sleep with different characteristics are repeated with a fixed rhythm, namely four to five times per night in an approximately 90-minute cycle. In this way, the depth of sleep of a person varies in an approximately 90-minute cycle. In the following, temporal variation in a depth of sleep during a night is referred to as a sleep cycle.

As described above, the microphone 70 converts sound that includes ambient sound N and playback sound P into a sound signal S, and provides the sound signal S to the A/D converter 271. The A/D converter 271 converts the sound signal S from analog format to digital format, and outputs the digital sound signal S to the echo canceller 270.

The echo canceller 270 outputs an ambient sound signal S1 that indicates the ambient sound N based on the sound signal S and the second playback sound signal P2. The sound signal S here is a signal that is converted into a digital signal after being output from the microphone 70, into which the ambient sound N and the playback sound P derived from the second playback sound signal P2 are input. The echo canceller 270, for example, subtracts the second playback sound signal P2 from the digital-converted sound signal S to generate the ambient sound signal S1, and outputs the ambient sound signal S1 to the adjuster 260.

The playback controller 240 specifies a piece of sound information to be played from among multiple pieces of sound information stored in the sound information table 251.

The playback controller 240 generates a personal profile of the human subject E when the human subject E first uses the system 1, and stores the personal profile of the human subject E in the personal table 252 of the storage device 250. In order to improve a quality of sleep of the human subject E by use of sound, it is a requisite that the human subject E is able to properly hear sound. Accordingly, information on the hearing ability of the human subject E (volume information and sound quality information) is measured. The playback controller 240 stores the information on the hearing ability of the human subject E in the personal table 252.

Based on the result of the hearing ability measurement performed in advance, playback of sound information is controlled. The hearing ability of the human subject E is measured by a test that tests whether the human subject E in a sleep position is able to hear sound output from the loudspeaker 51 that is installed in a bedroom under a condition in which the playback controller 240 controls the adjuster 260 such that the volume of sound output from the loudspeaker 51 changes. More specifically, hearing ability is measured by a test in which the human subject E presses a button when sound output from the loudspeaker 51 becomes inaudible under a condition in which the volume of the sound output from the loudspeaker 51 is continuously changing. Alternatively, there may each be measured a volume of sound from the loudspeaker 51 at a point where the sound output from the loudspeaker 51 becomes inaudible to the human subject E under a condition in which the volume of the sound output from the loudspeaker 51 is continuously decreasing, and a volume of sound from the loudspeaker 51 at a point where the sound output from the loudspeaker 51 becomes audible to the human subject E under a condition in which the volume of the sound output from the loudspeaker 51 is continuously increasing. Next, a reasonable average based on a comparison between these two values is used as a hearing ability measurement result. Alternatively, sounds with different volumes may be separately played, and the hearing ability may be estimated by the number of sounds, among the played sounds, that were audible to the human subject E. The playback controller 240 uses the measured value of the hearing ability of the human subject E to correct a standard volume of sound information when played, such that the volume of sound output from the loudspeaker 51 is at a volume audible to the human subject E. Similarly, frequency characteristics of the hearing ability of the human subject E are measured by a test that measures the hearing ability of the human subject E using different frequencies, and a sound quality of playback sound P is adjusted based on the measurement result.

In summary, the playback controller 240 adjusts the volume and sound quality of the playback sound P in accordance with a hearing ability of the human subject E by controlling the adjuster 260 based on the measurement result of the hearing ability of the human subject E. More specifically, the playback controller 240 outputs a first control signal C1 for controlling a sound quality and a second control signal C2 for controlling a volume. The first control signal C1 specifies a frequency characteristic to be set, and the second control signal C2 specifies a volume to be set.

Such adjustment is modified in accordance with the result of measurement whether the human subject E in an actual sleep position is able to hear sound output from the loudspeaker 51. As a result, such adjustment includes adjustment according to acoustic characteristics of devices and characteristics of a sound field environment. In other words, it is possible to correct playback sound in accordance with hearing ability characteristics of the human subject E, acoustic characteristics, and environmental characteristics.

Next, the sound signal generator 40 outputs a first playback sound signal P1 based on the sound information specified by the playback controller 240. The adjuster 260 adjusts the amplitude and frequency characteristics of the first playback sound signal P1 to output a second playback sound signal P2.

Figure 4:
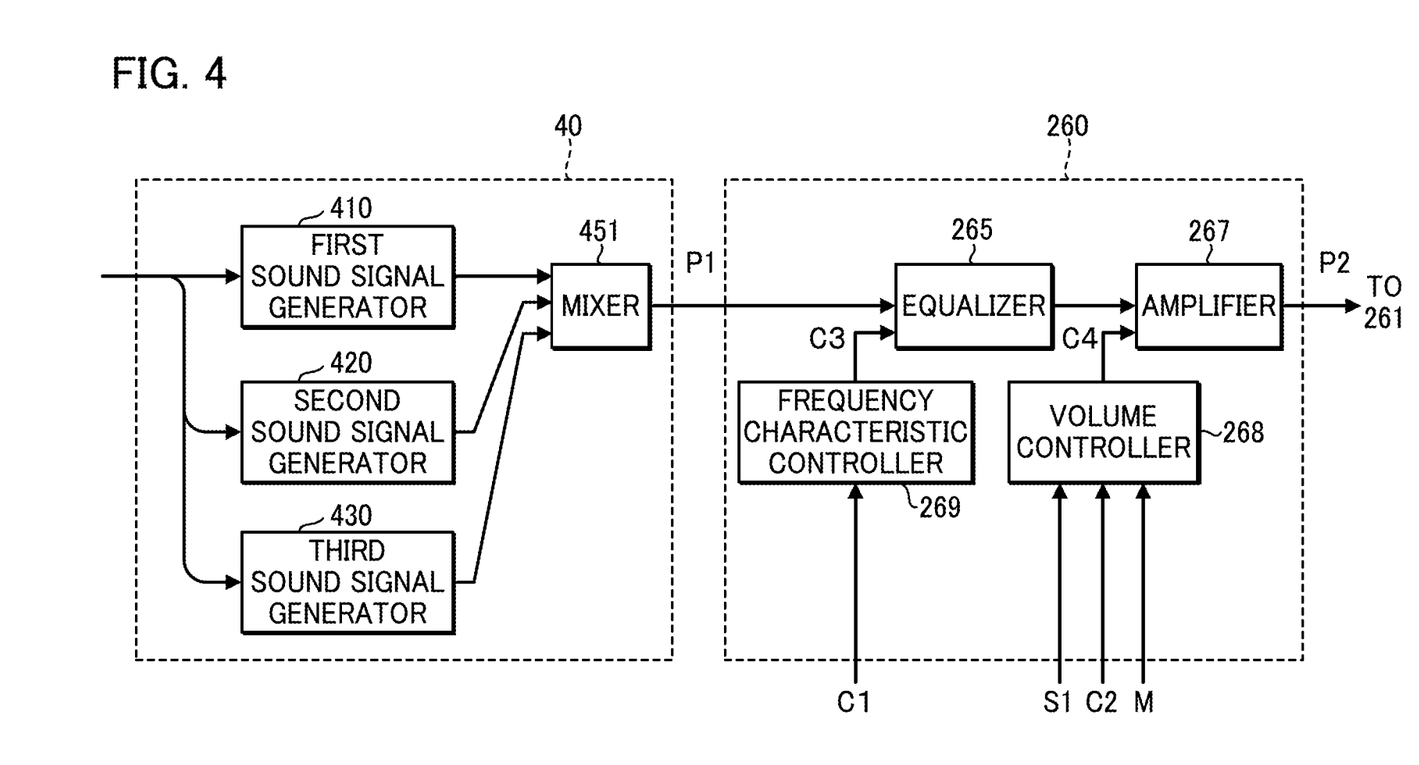
FIG. 4 is a block diagram showing an exemplary configuration of a sound signal generator and that of an adjuster.

FIG. 4 shows a detailed configuration of the sound signal generator 40 and of the adjuster 260. The sound signal generator 40 includes a first sound signal generator 410, a second sound signal generator 420, a third sound signal generator 430, and a mixer 451. The first sound signal generator 410 repeatedly generates a breathing-linked sound signal at a cycle linked to the breathing cycle BRm using information indicative of breathing-linked sound.

The second sound signal generator 420 repeatedly generates a heartbeat-linked sound signal at a cycle linked to the heartbeat cycle HRm using information indicative of heartbeat-linked sound. The third sound signal generator 430 repeatedly generates a background sound signal at a cycle linked to neither the breathing cycle BRm nor the heartbeat cycle HRm. In the following description, sound in accordance with a background sound signal that is generated at time intervals unrelated to biological cycles, such as the breathing cycle BRm and the heartbeat cycle HRm, may be referred to as "background sound". Examples of such background sound include a sound of sea waves, a sound of wind, a sound of a stream, and a sound of a crowd. As will be understood, the sound information includes three elements: information indicative of heartbeat-linked sound, information indicative of breathing-linked sound, and information indicative of background sound. A fourth sound signal generator may further be provided, and the fourth sound signal generator may generate information indicative of music.

The first to third sound signal generators 410 to 430 switch sound information (e.g., information indicative of heartbeat-linked sound, information indicative of breathing-linked sound, and information indicative of background sound) that is to be retrieved from the sound information table 251 of the storage device 250, from one sound information to another at a timing specified by the playback controller 240. Using the retrieved sound information, the first to third sound signal generators 410 to 430 output stereo two-channel sound signals in digital format. The mixer 451 mixes (adds) the sound signals output from the first to third sound signal generators 410 to 430 to output a first playback sound signal P1.

The adjuster 260 includes an equalizer 265, an amplifier 267, a volume controller 268, and a frequency characteristic controller 269. The equalizer 265 applies a frequency characteristic to the first playback sound signal P1. The amplifier 267 is an example of a volume adjuster that generates a second playback sound signal P2 by adjusting the amplitude of the first playback sound signal P1. The amplifier 267 amplifies the first playback sound signal P1 to which the frequency characteristic has been applied to generate the second playback sound signal P2.

The frequency characteristic controller 269 controls the equalizer 265 such that the frequency characteristic of the first playback sound signal P1 is set to be the frequency characteristic specified by the first control signal C1. For example, in a case where the human subject E is an elderly person and that person has difficulty in hearing high-pitched sound, the frequency characteristic controller 269 controls the equalizer 265 such that, with regard to the first playback sound signal P1, a frequency of 1.5 KHz is emphasized by 3 dB and a frequency of 2 KHz is emphasized by 5 dB. The frequency characteristic controller 269 controls the equalizer 265 using a third control signal C3 that sets the frequency characteristic of the first playback sound signal P1 to match the frequency characteristic specified by the first control signal C1.

The volume controller 268 identifies the volume (amplitude) of the ambient sound N based on the ambient sound signal S1. More specifically, the volume controller 268 acquires the volume of the ambient sound based on the ambient sound signal S1. Then, the volume controller 268 controls a gain of the amplifier 267 such that the volume of the playback sound P is higher than the volume of the ambient sound N. In this way, the amplifier 267 is able to output the second playback sound signal P2 in which the amplitude of the first playback sound signal P1 has been adjusted. Here, the greater the amplitude of the second playback sound signal P2, the higher the volume of the playback sound P. The volume controller 268 controls a gain of the amplifier 267 based on the sleep indicator M indicating the depth of sleep. More specifically, the volume controller 268 controls the gain of the amplifier 267 such that, in at least a portion of the period of a sleep, the volume of the playback sound P is higher than the volume of the ambient sound N, and as a depth of sleep indicated by the sleep indicator M becomes shallower, a difference between the volume of the playback sound P and that of the ambient sound N becomes smaller. After controlling the gain as described above, the volume controller 268 further controls the gain of the amplifier 267 based on the second control signal C2.

Figure 5:
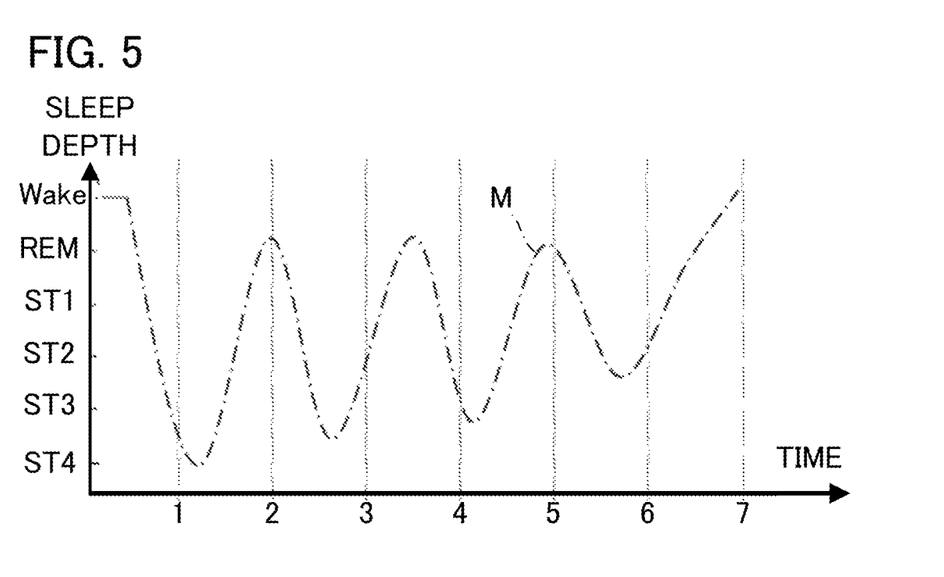
FIG. 5 is a graph showing changes in a sleep indicator during sleep.
Figure 6:
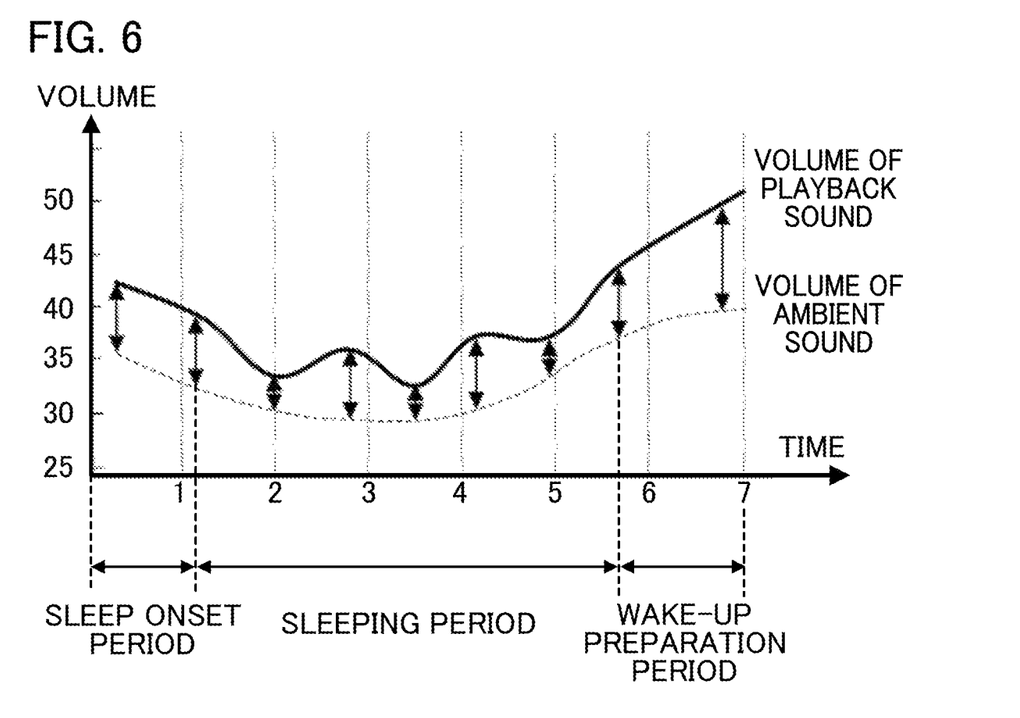
FIG. 6 is a graph showing a relationship between a volume of ambient sound and a volume of playback sound.

With reference to FIG. 5 and FIG. 6, gain control based on the sleep indicator M will now be described. FIG. 5 is a graph that shows changes in the sleep indicator M during sleep. FIG. 6 is a graph that shows a relationship between a volume of ambient sound N and a volume of playback sound P. As shown in FIG. 5, the sleep indicator M changes in multiple cycles during sleep. When the sleep indicator M indicates deep sleep, it is unlikely that the human subject E will wake up even if a volume of sound output from the loudspeaker 51 is high. When the sleep indicator M indicates light sleep, it is likely that the human subject E will wake up even if the volume of sound output from the loudspeaker 51 is low. In view of this, the volume controller 268 uses the volume of the ambient sound N as a standard in a sleep onset period, and controls the amplifier 267 such that a volume of the playback sound P is higher than the standard by a preset volume. Additionally, the volume controller 268 controls a gain of the amplifier 267 such that, during a sleeping period, a volume of the playback sound P is higher than the standard, and as the depth of sleep indicated by the sleep indicator M becomes shallower, a difference between the volume of the playback sound P and the volume of the ambient sound N becomes smaller. The volume controller 268 further controls the gain of the amplifier 267 such that, in a wake-up preparation period, the volume of the playback sound P is higher than the standard, and the difference between the volume of the playback sound P and the volume of the ambient sound N becomes gradually greater with time. With use of the fourth control signal C4 that causes the amplifier 267 to operate in the above-described way, the volume controller 268 controls the amplifier 267.

Since the volume of the playback sound P is higher than the volume of the ambient sound N by the preset volume in the sleep onset period, inconvenience can be lessened that the human subject E is unable to hear the playback sound P due to the ambient sound N. During the sleeping period, the difference between the volume of the playback sound P and that of the ambient sound N is controlled according to a depth of sleep. Thus, the human subject E can be prevented from waking up when his/her sleep is light. Since the human subject E is able to hear the playback sound P when his/her sleep is deep, the human subject E can be induced into good sleep. In the wake-up preparation period, the human subject E can be induced into wakefulness.

Figure 7:
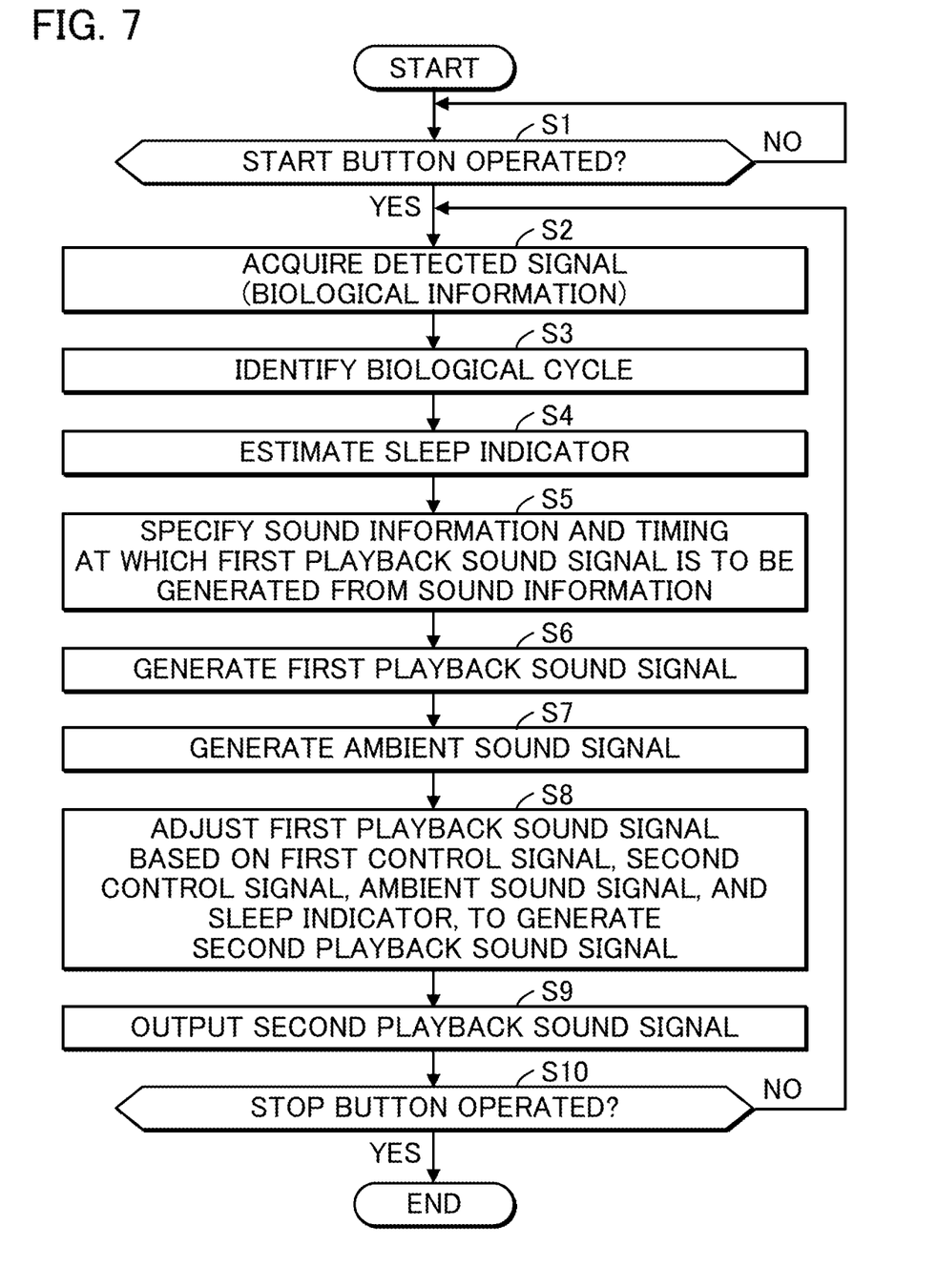
FIG. 7 is a flowchart for describing an operation of the information processing apparatus.

FIG. 7 is a flowchart showing operations of the information processing apparatus 20.

Firstly, the playback controller 240 determines whether the start button has been operated (step S1). If the determination result is positive, the acquirer 210 acquires a detected signal (biological information) that has been converted into a digital signal by the A/D converter 205 (step S2). Next, the biological cycle identifier 220 identifies biological cycles (breathing cycle BRm and heartbeat cycle HRm) of the human subject E based on the biological information included in the detected signal (step S3). The estimator 230 then estimates the sleep indicator M1 of the human subject E based on the breathing cycle BRm, the heartbeat cycle HRm, and the biological information (step S4).

Then, the playback controller 240 specifies sound information, and specifies a timing at which a first playback sound signal is to be generated from the sound information based on the breathing cycle BRm and the heartbeat cycle HRm (step S5). The playback controller 240 generates a first control signal C1 and a second control signal C2 based on the information on the hearing ability of the human subject E that is stored in the personal table 252. The playback controller 240 outputs the first control signal C1, the second control signal C2, and the sleep indicator M1, to the adjuster 260.

Then, the sound signal generator 40 retrieves the sound information specified by the playback controller 240 from the sound information table 251 at the timing specified by the playback controller 240. The sound signal generator 40 then generates a first playback sound signal P1 using the retrieved sound information (step S6).

Then, the echo canceller 270 subtracts a second playback sound signal P2 from a sound signal S (sound signal S output from the microphone 70) that has been converted into a digital signal by the A/D converter 271, to generate an ambient sound signal S1 (step S7). In a case where the second playback sound signal P2 has not been generated, the echo canceller 270 outputs the sound signal S as the ambient sound signal S1.

Then, the adjuster 260 adjusts the first playback sound signal P1 based on the first control signal C1, the second control signal C2, the sleep indicator M1, and the ambient sound signal S1, to generate a second playback sound signal P2 (step S8).

At step S8, the frequency characteristic controller 269 controls the equalizer 265 such that a frequency characteristic of the first playback sound signal P1 is set to be a frequency characteristic specified by the first control signal C1. Then, the volume controller 268 identifies the volume of the ambient sound N based on the ambient sound signal S1. The volume controller 268 then controls a gain of the amplifier 267 such that the volume of the playback sound P, which is in accordance with the second playback sound signal P2, is higher than the volume of the ambient sound N. In this way, the amplifier 267 generates the second playback sound signal P2 in which the amplitude of the first playback sound signal P1 has been adjusted.

Then, the amplifier 267 outputs the second playback sound signal P2 to the D/A converter 261. The D/A converter 261 converts the second playback sound signal P2 into an analog signal, and outputs the analog second playback sound signal P2 to the loudspeaker 51 (step S9). The loudspeaker 51 outputs playback sound P that is in accordance with the analog second playback sound signal P2.

Then, the playback controller 240 determines whether the stop button has been operated (step S10). If the determination result at step S10 is negative, the playback controller 240 returns the processing to step S2. If the determination result at step S10 is positive, the playback controller 240 ends the processing.

Second Embodiment

Next, a second embodiment of the invention will be described. An information processing apparatus 20 in the second embodiment is configured in a manner similar to the information processing apparatus 20 in the first embodiment, except for use of an adjuster 260A instead of the adjuster 260.

Figure 8:
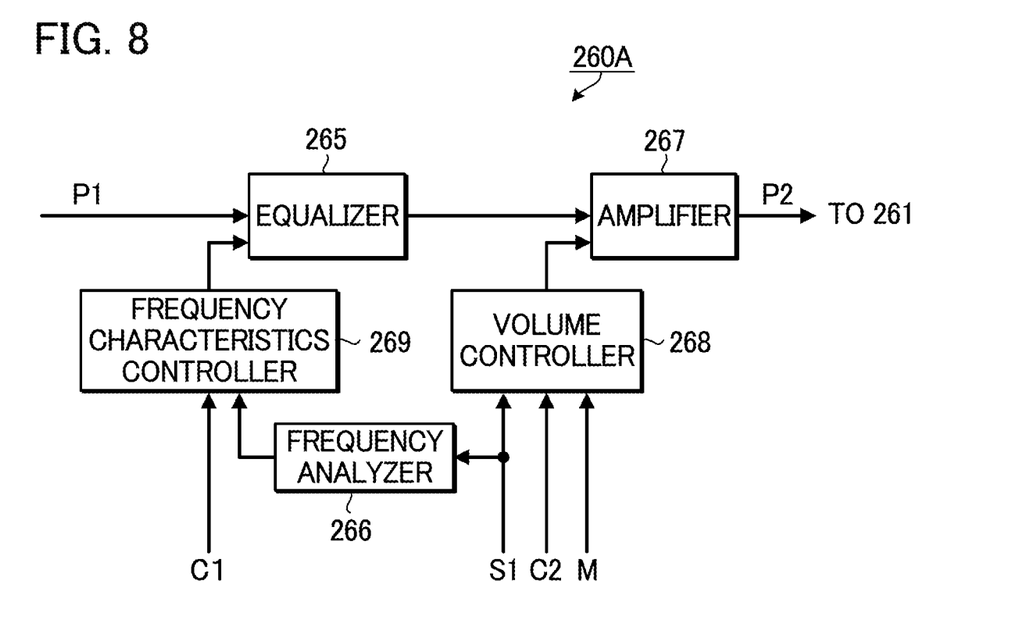
FIG. 8 is a block diagram showing a configuration of an adjuster according to a second embodiment.

FIG. 8 shows a configuration of the adjuster 260A in the second embodiment. The adjuster 260A includes a frequency analyzer 266 in addition to the elements included in the adjuster 260. The frequency analyzer 266 executes frequency analysis on the ambient sound signal S1 to identify the frequency spectrum of the ambient sound N. The frequency characteristic controller 269 controls the equalizer 265 such that the frequency spectrum of the playback sound P is higher than the frequency spectrum of the ambient sound N within an audible band.

More specifically, for each of multiple pieces of sound information, the sound information table 251 associates spectrum data showing a frequency spectrum of sound information with the sound information, and stores the spectrum data. The playback controller 240, when selecting sound information, retrieves spectrum data corresponding to the selected sound information, and provides the adjuster 260A with the retrieved spectrum data. The frequency characteristic controller 269 compares the spectrum data with the analysis result by the frequency analyzer 266, and controls equalizer 265 such that the frequency spectrum of the playback sound P is higher than the frequency spectrum of the ambient sound N within the audible band.

Figure 9:
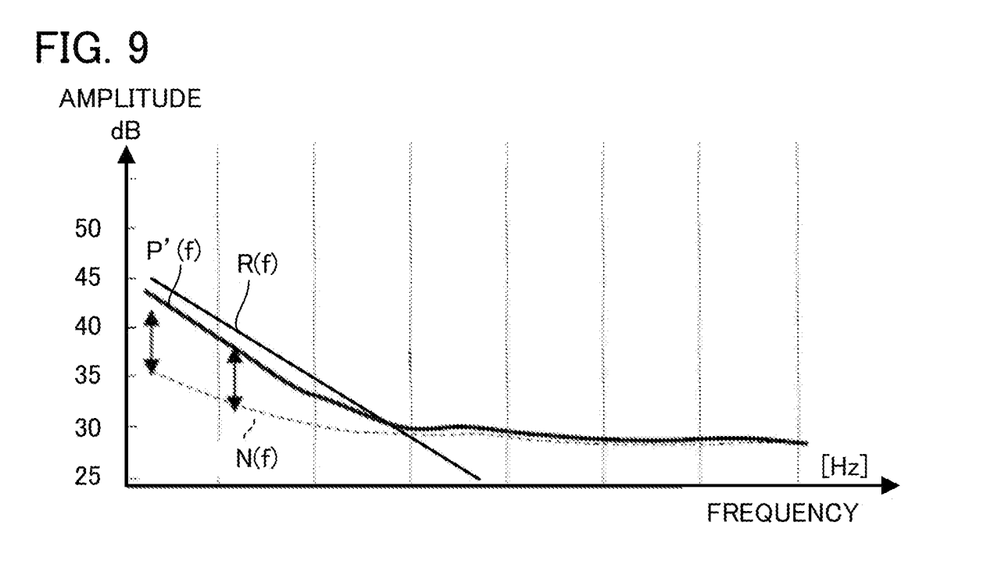
FIG. 9 is a graph showing an exemplary relationship between the frequency spectrum of ambient sound, the frequency spectrum of corrected playback sound, and a 1/f characteristic.

In order not to disturb good sleep, it is preferable that the frequency spectrum of sound to be heard by the human subject E be lower than a frequency spectrum showing a 1/f characteristic (where f is a frequency). In view of this, the frequency characteristic controller 269 may control the equalizer 265 such that the frequency spectrum of the playback sound P does not exceed the frequency spectrum showing a 1/f characteristic. Details will be described with reference to FIG. 9. It is assumed that the frequency spectrum of the ambient sound N is indicated by N(f), the frequency spectrum of 1/f is indicated by R(f), the frequency spectrum of the playback sound P before being corrected is indicated by P(f), and the frequency spectrum of the playback sound P after being corrected is indicated by P'(f) (in FIG. 9, illustration of the frequency spectrum P(f) is omitted). Here, in a case where N(f)≥P(f), the frequency characteristic controller 269 controls the equalizer 265 such that P'(f)>N(f) and R(f)>P'(f). In a case where N(f)≥P(f), the frequency characteristic controller 269 may control the equalizer 265 such that P'(f)=(R(f)+P(f))/2. In a case where N(f)<P(f), the frequency characteristic controller 269 controls the equalizer 265 such that R(f)>P'(f).

As described above, in the present embodiment, the frequency spectrum of the ambient sound N is identified, and frequency characteristics to be applied to the first playback sound signal P1 are controlled such that the frequency spectrum of the playback sound P is higher than the frequency spectrum of the ambient sound N within the audible band. In this way, even when ambient sound N can be heard, the human subject E is still able to hear the playback sound P. As a result, a quality of sleep of the human subject E can be improved.

Modifications

The present invention is not limited to the above-described embodiments, and various applications or modifications, such as those described in the following, are possible.

Modification 1

In the above-described embodiments, biological information of the human subject E is detected using a sheet-like sensor 11. However, the present invention is not limited to this example. The sensor 11 may be any sensor that can detect the biological information. For example, an electrode of a first sensor may be attached to the forehead of the human subject E, and brain waves (e.g., $\alpha$-wave, $\beta$-wave, $\delta$-wave, and $\theta$-wave) of the human subject E may be detected by the first sensor. A second sensor may be attached to a wrist of the human subject E, and pressure changes in, for example, the radial artery may be detected by the second sensor (i.e., a pulse wave may be detected by the second sensor). Since the pulse wave is synchronized with a heartbeat, detection of the pulse wave represents indirect detection of the heartbeat. There may be provided between the head of the human subject E and a pillow a third sensor that detects acceleration, and body motion of the human subject E, such as breathing and heartbeat, may be detected by the third sensor. The types of sensors for detecting the biological information may be any of pressure, air pressure, vibration, optical, ultrasound Doppler, RF Doppler, or laser Doppler.

Modification 2

In the above-described embodiments, the first control signal C1 and the second control signal C2 are provided to the adjuster 260 in order to correct the first playback sound signal in accordance with the hearing ability of the human subject. However, the present invention is not limited to this example, and the first playback sound signal need not be corrected in accordance with the hearing ability of the human subject. In this mode, the volume of the playback sound can be adjusted not only in view of the depth of sleep of the human subject, but also in view of the volume of ambient sound.

Modification 3

In the above-described embodiments and modifications, signal processing is performed in which the sound signal generator 40 of the information processing apparatus 20 generates the first playback sound signal P1 based on the sound information retrieved from the sound information table 251, and the equalizer 265 and the amplifier 267 of the information processing apparatus 20 adjust the first playback sound signal P1 to generate the second playback sound signal P2. However, the present invention is not limited to this example. For example, part of the functions of the information processing apparatus 20 may be provided by a server device that is connected to a communication network (i.e., may be provided in the so-called cloud), the sound signal generator 40 of an information processing apparatus connected to the server device via the communication network may generate the first playback sound signal P1, and the equalizer 265 and the amplifier 267 of the information processing apparatus may adjust the first playback sound signal P1 to generate the second playback sound signal P2.

Figure 10:
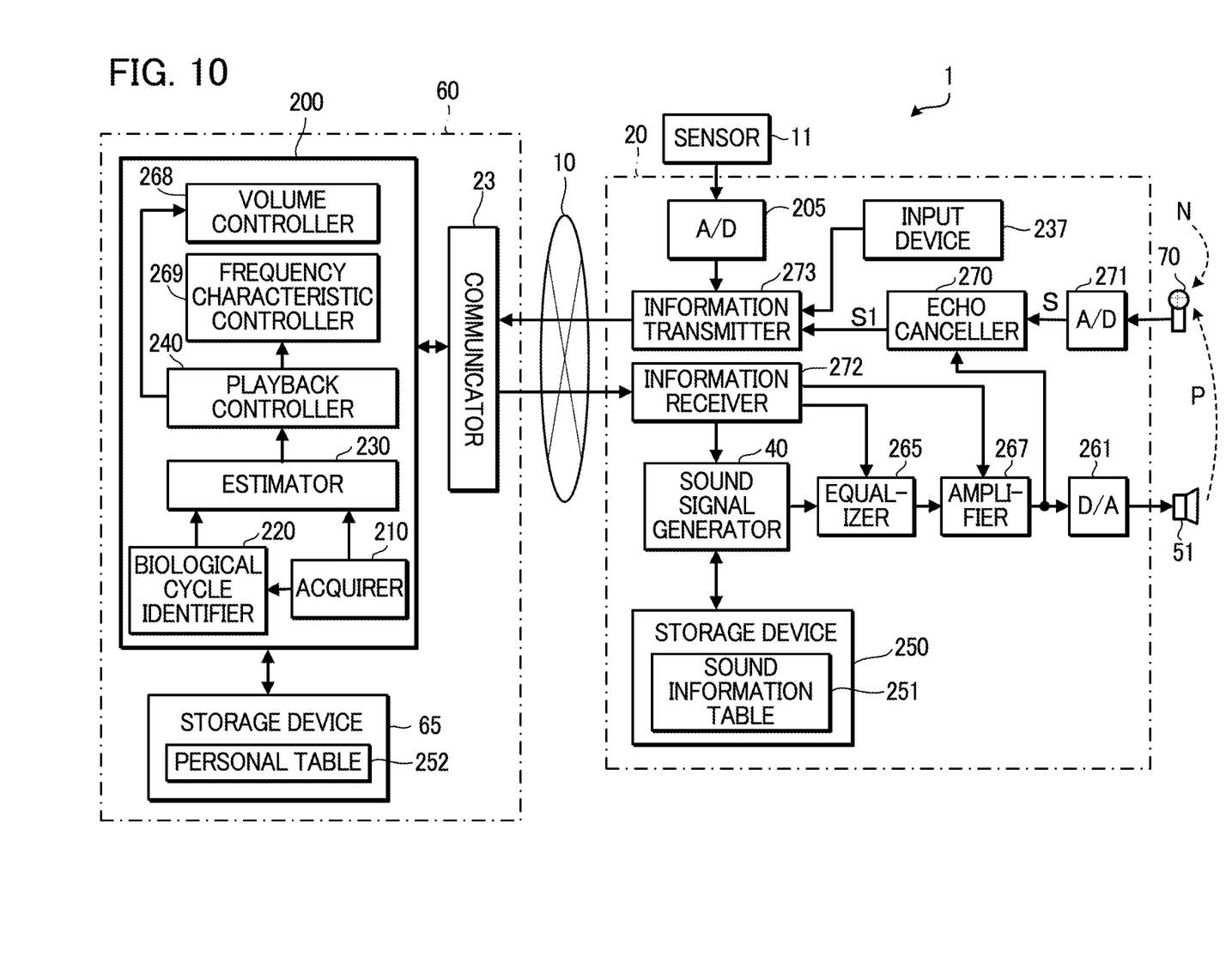
FIG. 10 is an illustration showing an overall configuration of a system according to a modification.

FIG. 10 shows an exemplary configuration according to modification 3. As shown in FIG. 10, from among the functional elements provided in the information processing apparatus 20 in the above embodiments, the acquirer 210, the biological cycle identifier 220, the estimator 230, the playback controller 240, the volume controller 268, and the frequency characteristic controller 269 are provided instead in a server device 60 in the system 1 of the present modification. Additionally, the server device 60 includes a storage device 65 that stores the personal table 252, which is stored in the storage device 250 in the above embodiments, and a communicator 23 for communicating with the information processing apparatus 20 via a communication network 10.

The information processing apparatus 20 in the present modification includes an information transmitter 273 and an information receiver 272, instead of the acquirer 210, the biological cycle identifier 220, the estimator 230, the playback controller 240, the volume controller 268, and the frequency characteristic controller 269. The information transmitter 273 transmits, to the server device 60 via the communication network 10, the detected signal from the sensor 11 and the ambient sound signal S1 from the echo canceller 270. Additionally, the information transmitter 273 transmits, to the server device 60 via the communication network 10, operation information (e.g., start-operation information indicating an operation of the start button and stop-operation information indicating an operation of the stop button) received by the input device 237.

The information receiver 272 receives information (sound-information specifying information that specifies the sound information, timing specifying information that specifies the timing at which the first playback sound signal is to be generated, the third control signal C3, and the fourth control signal C4) from the playback controller 240, the volume controller 268, and the frequency characteristic controller 269 of the server device 60 via the communicator 23 and the communication network 10. The information receiver 272 outputs the sound-information specifying information and the timing specifying information to the sound signal generator 40. The information receiver 272 outputs the third control signal C3 to the equalizer 265. The information receiver 272 outputs the fourth control signal C4 to the amplifier 267.

The storage device 250 of the information processing apparatus 20 in the present modification does not store the personal table 252, but stores the sound information table 251.

In the present modification, like elements are denoted by the same reference signs as like elements in the above embodiments, and description thereof is omitted, as appropriate.

In the configuration shown in FIG. 10, the detected signal from the sensor 11 is transmitted from the information processing apparatus 20 to the server device 60, and in the server device 60, the acquirer 210, the biological cycle identifier 220, the estimator 230, the playback controller 240, the volume controller 268, and the frequency characteristic controller 269 execute processing similar to that described in the above embodiments.

The information processing apparatus 20 retrieves sound information from the storage device 250 in accordance with the sound-information specifying information and the timing specifying information received from the server device 60, and generates a first playback sound signal P1 that is based on the retrieved sound information. Then, in accordance with the third control signal C3 and the fourth control signal C4 received from the server device 60, the information processing apparatus 20 generates a second playback sound signal P2 by adjusting the first playback sound signal P1.

In the configuration shown in FIG. 10, step S1, steps S6 to S7, and steps S9 to S10 shown in FIG. 7 are performed by the information processing apparatus 20, and steps S2 to S5 are performed by the server device 60. With respect to step S8, generation of the control signals C3 and C4 is performed by the server device 60, and the operation to generate the second playback sound signal P2 by adjusting the first playback sound signal P1 based on the control signals C3 and C4 is performed by the information processing apparatus 20.

Instead of the configuration shown in FIG. 10, a configuration may be used in which the sound information table 251 and the sound signal generator 40 are provided in the server device 60, instead of in the information processing apparatus 20. Additionally, the equalizer 265 and the amplifier 267 may be provided in the server device 60. In this case, the second playback sound signal P2 is transmitted to the information processing apparatus 20 via the communicator 23. Furthermore, elements in the server device 60 may be dispersed across multiple server devices. Additionally or alternatively, the information processing apparatus 20 may be provided with part of the functions of the server device 60 (one or more among the acquirer 210, the biological cycle identifier 220, the estimator 230, the playback controller 240, the volume controller 268, and the frequency characteristic controller 269). In any of the above-mentioned configurations, advantageous effects similar to those in the above embodiments are achieved.

As will be understood from the above description, the information processing apparatus 20 that includes the estimator 230, the playback controller 240, the volume controller 268, and the frequency characteristic controller 269, is an example of a sound signal controlling apparatus, and the server device 60 that includes these elements is another example of the sound signal controlling apparatus.

The following inventions may be understood from the above-described embodiments and modifications.

A mode of a sound signal controlling apparatus according to the present invention includes: an estimator configured to estimate, based on biological information of a human subject, a sleep indicator indicative of a depth of sleep of the human subject; and a volume controller configured to control, based on the sleep indicator and a volume of ambient sound in an environment in which the human subject is situated, adjustment of an amplitude of a first playback sound signal in a volume adjuster that generates a second playback sound signal by adjusting the amplitude of the first playback sound signal.

In this mode, the amplitude of the second playback sound signal can be adjusted in accordance with, not only the depth of sleep of the human subject, but also the volume of the ambient sound.

Preferably, the sound signal controlling apparatus further includes a generator configured to generate an ambient sound signal indicative of the ambient sound based on the second playback sound signal and a sound signal, wherein the sound signal is output from a microphone into which the ambient sound and playback sound derived from the second playback sound signal are input. The volume controller preferably identifies the volume of the ambient sound based on the ambient sound signal.

The microphone receives sound in which the playback sound derived from the second playback sound signal and the ambient sound are superimposed. The received sound is audible to the human subject.

In this mode, the generator generates the ambient sound signal based on the sound signal, which is in accordance with the sound in which the playback sound and the ambient sound are superimposed, and based on the second playback sound signal corresponding to the playback sound. Accordingly, it is possible to cancel the playback sound from the sound in which two kinds of sounds are superimposed to retrieve the ambient sound.

In this way, the volume of the ambient sound can be identified, and thus, it is possible to prevent the playback sound from becoming unnecessarily loud or too quiet.

Preferably, the volume controller controls the adjustment of the amplitude in the volume adjuster such that a volume of the playback sound is higher than the volume of the ambient sound and a difference between the volume of the playback sound and the volume of the ambient sound becomes smaller as the depth of sleep indicated by the sleep indicator becomes shallower.

In this mode, since the adjustment of the amplitude is controlled such that the volume of the playback sound is higher than the volume of the ambient sound, a situation can be improved in which the human subject is unable to hear the playback sound due to the ambient sound.

Furthermore, during a part of a period of sleep, the adjustment is controlled such that as the depth of sleep becomes shallower, the difference between the volume of the playback sound and the volume of the ambient sound becomes smaller. Thus, while the sleep of the human subject is light, it is possible to allow the human subject to hear the playback sound and still reduce the possibility of wakening the human subject.

In a case where a sleep is divided into a sleep onset period, a wake-up preparation period, and a sleeping period, the part of the period of sleep preferably overlaps with at least the sleeping period, wherein the sleep onset period is from a point at which the human subject goes to bed to a point at which the depth of sleep reaches deep sleep, the wake-up preparation period is a period during which the depth of sleep becomes shallower toward awakening, and the sleeping period is from the end of the sleep onset period to the beginning of the wake-up preparation period.

Preferably, the sound signal controlling apparatus further includes: a generator configured to generate an ambient sound signal indicative of the ambient sound based on the second playback sound signal and a sound signal, wherein the sound signal is output from a microphone into which the ambient sound and playback sound derived from the second playback sound signal are input; a frequency analyzer configured to execute frequency analysis on the ambient sound signal; and a frequency characteristic controller configured to adjust, based on a result of the frequency analysis by the frequency analyzer, a frequency characteristic to be applied to the first playback sound signal such that a frequency spectrum of the playback sound is higher than a frequency spectrum of the ambient sound within an audible band.

In this mode, a frequency analysis is executed on the ambient sound signal, and a frequency characteristic to be applied to the first playback sound signal is adjusted such that the frequency spectrum of the playback sound is higher than the frequency spectrum of the ambient sound. Accordingly, it is possible to output playback sound that can be heard with ease by the human subject.

The invention of the above-described sound signal controlling apparatus may be understood as an invention of a program for the sound signal controlling apparatus including a computer.

Such a program works in the following manner, for example.

The program causes the computer to execute: sleep indicator estimating processing of estimating, based on biological information of a human subject, a sleep indicator indicative of a depth of sleep of the human subject; and volume controlling processing of controlling, based on the sleep indicator and a volume of ambient sound in an environment in which the human subject is situated, adjustment of an amplitude of a first playback sound signal in a volume adjuster that generates a second playback sound signal by adjusting the amplitude of the first playback sound signal.

DESCRIPTION OF REFERENCE SIGNS

1 . . . system, 11 . . . sensor, 20 . . . information processing apparatus, 40 . . . sound signal generator, 51 . . . loudspeaker, 210 . . . acquirer, 220 . . . biological cycle identifier, 230 . . . estimator, 240 . . . playback controller, 260 . . . adjuster, 265 . . . equalizer, 266 . . . frequency analyzer, 267 . . . amplifier, 268 . . . volume controller, 269 . . . frequency characteristic controller.

What is claimed is:

1. A sound signal controlling apparatus comprising:
a memory storing instructions; and
a processor that implements the instructions to:
estimate, based on biological information of a human subject, a sleep indicator indicative of a depth of sleep of the human subject;
generate a playback sound signal for outputting playback sound;
generate an ambient sound signal indicative of ambient sound based on the generated playback sound signal and a sound signal output from a microphone disposed in an environment where the human subject is situated;
determine a volume of the ambient sound obtained from the generated ambient sound signal; and
control a volume of the playback sound obtained from the generated playback sound signal based on the estimated sleep indicator and the determined ambient sound volume.

2. The sound signal controlling apparatus according to claim 1, wherein the processor controls the volume of the playback sound to be higher than the volume of the ambient sound, and so that a difference between the volume of the playback sound and the volume of the ambient sound becomes smaller as the depth of sleep indicated by the sleep indicator becomes shallower.

3. The sound signal controlling apparatus according to claim 1, wherein the processor implements the instructions to:
execute frequency analysis on the ambient sound signal; and
adjust, based on a result of the frequency analysis, a frequency characteristic to be applied to the playback sound signal so that a frequency spectrum of the playback sound is higher than a frequency spectrum of the ambient sound within an audible band.

4. A sound signal controlling method comprising:
estimating, based on biological information of a human subject, a sleep indicator indicative of a depth of sleep of the human subject;
generating a playback sound signal for outputting playback sound;
generating an ambient sound signal indicative of ambient sound based on the generated playback sound signal and a sound signal output from a microphone disposed in an environment where the human subject is situated;
determining a volume of the ambient sound obtained from the generated ambient sound signal; and
controlling a volume of the playback sound obtained from the generated playback sound signal based on the estimated sleep indicator and the determined ambient sound volume.

5. A non-transitory computer-readable recording medium storing a program executable by a computer to execute a method comprising:
estimating, based on biological information of a human subject, a sleep indicator indicative of a depth of sleep of the human subject;
generating a playback sound signal for outputting playback sound;
generating an ambient sound signal indicative of ambient sound based on the generated playback sound signal and a sound signal output from a microphone disposed in an environment where the human subject is situated;
determining a volume of the ambient sound obtained from the generated ambient sound signal; and
controlling a volume of the playback sound obtained from the generated playback sound signal based on the estimated sleep indicator and the determined ambient sound volume.

* * * * *